United States Patent
Huddleston et al.

(10) Patent No.: US 12,279,856 B2
(45) Date of Patent: Apr. 22, 2025

(54) SYSTEMS AND METHODS FOR GENERATING BIOMARKERS BASED ON MULTIVARIATE MRI AND MULTIMODALITY CLASSIFIERS FOR DISORDER DIAGNOSIS

(71) Applicant: Emory University, Atlanta, GA (US)

(72) Inventors: Daniel Huddleston, Marietta, GA (US); Babak Mahmoudi, Alpharetta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 18/583,373

(22) Filed: Feb. 21, 2024

(65) Prior Publication Data
US 2024/0188843 A1  Jun. 13, 2024

Related U.S. Application Data

(63) Continuation of application No. 16/980,761, filed as application No. PCT/US2019/022229 on Mar. 14, 2019, now abandoned.
(Continued)

(51) Int. Cl.
*A61B 5/055*  (2006.01)
*A61B 5/00*  (2006.01)
(Continued)

(52) U.S. Cl.
CPC ............ *A61B 5/055* (2013.01); *A61B 5/0042* (2013.01); *A61B 5/4082* (2013.01);
(Continued)

(58) Field of Classification Search
CPC . A61B 5/055; A61B 5/0042; A61B 2576/026; A61B 5/7264; G16H 70/60;
(Continued)

(56) References Cited

U.S. PATENT DOCUMENTS

2008/0312513 A1   12/2008  Simon et al.
2009/0247910 A1   10/2009  Klapper
(Continued)

FOREIGN PATENT DOCUMENTS

CN   106485707 A   3/2017
EP     2955536 A1  12/2015
(Continued)

OTHER PUBLICATIONS

C. Zheng et al, "Automated identification of dementia using medical imaging: a survey from a pattern classification perspective", Brain Informatics, vol. 3, pp. 17-27, Dec. 2015 (Year: 2015).*
(Continued)

*Primary Examiner* — Joel Lamprecht
*Assistant Examiner* — Nyrobi Celestine
(74) *Attorney, Agent, or Firm* — Emory Patent Group

(57) ABSTRACT

In some embodiments, the systems and methods of the disclosure can efficiently and accurately classify neurodegenerative disorder(s) and/or movement disorder(s) of a subject (e.g., a patient) using at least quantitative features associated with one or more regions of interest determined from one or more sets of image data of the subject's brain. The method may include processing one or more sets of MRI image data of the subject's brain to extract one or more quantitative features for one or more regions. The one or more quantitative features may include a first quantitative and a second quantitative feature. The method may further include classifying at least the one or more quantitative features into one or more classes associated with neurodegenerative dementia disorder, neurodegenerative movement disorder, non-neurodegenerative movement disorder and/or heathy control. The method may include generating a report including a classification of at least the one or more quantitative features.

21 Claims, 8 Drawing Sheets

Related U.S. Application Data

(60) Provisional application No. 62/737,471, filed on Sep. 27, 2018, provisional application No. 62/642,782, filed on Mar. 14, 2018.

(51) Int. Cl.

| | | |
|---|---|---|
| *G01R 33/56* | (2006.01) | |
| *G06F 18/2431* | (2023.01) | |
| *G06T 7/00* | (2017.01) | |
| *G06V 10/25* | (2022.01) | |
| *G16H 10/20* | (2018.01) | |
| *G16H 15/00* | (2018.01) | |
| *G16H 30/40* | (2018.01) | |
| *G16H 50/20* | (2018.01) | |
| *G16H 70/60* | (2018.01) | |

(52) U.S. Cl.
CPC ........ *A61B 5/7264* (2013.01); *G01R 33/5608* (2013.01); *G06F 18/2431* (2023.01); *G06T 7/0012* (2013.01); *G06V 10/25* (2022.01); *G16H 10/20* (2018.01); *G16H 15/00* (2018.01); *G16H 30/40* (2018.01); *G16H 50/20* (2018.01); *G16H 70/60* (2018.01); *A61B 5/7267* (2013.01); *A61B 2576/026* (2013.01); *G06T 2207/10088* (2013.01); *G06T 2207/30016* (2013.01)

(58) Field of Classification Search
CPC .......... G16H 50/20; G06T 2207/30016; G06T 2207/10088; G06T 7/0012; G01R 33/4806
See application file for complete search history.

(56) References Cited

U.S. PATENT DOCUMENTS

| | | | |
|---|---|---|---|
| 2010/0016706 A1 | 1/2010 | Wohlgemuth | |
| 2013/0028489 A1 | 1/2013 | Tracton et al. | |
| 2015/0125057 A1* | 5/2015 | Huddleston | G06T 7/0012 382/131 |
| 2018/0204327 A1* | 7/2018 | Matthews | A61B 5/7275 |
| 2018/0206774 A1 | 7/2018 | Huang | |
| 2019/0117072 A1* | 4/2019 | Pereira | G06T 3/14 |
| 2020/0288980 A1* | 9/2020 | Stern | G16H 50/70 |

FOREIGN PATENT DOCUMENTS

| | | | |
|---|---|---|---|
| WO | WO 2013165573 A1 | 11/2013 | |
| WO | WO-2016016459 A1 * | 2/2016 | ........... G06F 19/321 |
| WO | WO 2017011746 | 1/2017 | |

OTHER PUBLICATIONS

X. Chen et al, "Simultaneous imaging of locus coeruleus and substantia nigra with a quantitative neuromelanin MRI approach", Magnetic Resonance Imaging, vol. 32, pp. 1301-1306, Jul. 2014 (Year: 2014).*

Langkammer et al, "Quantitative Susceptibility Mapping in Parkinson's Disease", PLOS One, vol. 11, No. 9, pp. 1-13, Sep. 2016 (Year: 2016).*

D. Huddleston et al, "In Vivo Detection of Lateral-Ventral Tier Nigral Degeneration in Parkinson's Disease", Human Brain Mapping, vol. 38, pp. 2627-2634, 2017 (Year: 2017).*

J. Barbosa et al, "Quantifying brain iron deposition in patients with Parkinson's disease using quantitative susceptibility mapping, R2 and R2*", Magnetic Resonance Imaging, vol. 33, pp. 559-565, 2015 (Year: 2015).*

J. Langley et al, "Reproducibility of locus coeruleus and substantia nigra imaging with neuromelanin sensitive MRI", Magnetic Resonance Materials in Physics, Biology and Medicine (MAGMA), vol. 30, No. 2, pp. 121-125, Apr. 2017 (Year: 2017).*

J. Langley et al, "Parkinson's Disease-Related Increase of T 2-Weighted Hypointensity in Substantia Nigra Pars Compacta", Movement Disorders, vol. 32, No. 3, pp. 441-449, 2017 (Year: 2017).*

Ellis et al. "A Cloud-based Framework for Implementing Portable Machine Learning Pipelines for Neural Data Analysis." Annual International Conference of the IEEE Engineering in Medicine and Biology Society. Jul. 2019; 2019:4466-4469.

Huddleston et al. "In vivo detection of lateral-ventral tier nigral degeneration in Parkinson's disease." Human Brain Mapping. 2017; 38:2627-2634.

Langley et al. "Parkinson's disease-related increase of T2*-weighted hypointensity in substantia nigra pars compacta." Movement Disorders. 2017; 32:441-449.

Lui et al. "Classification algorithms using multiple MRI features in mild traumatic brain injury." Neurology. 2014; 83:1235-40.

Extended European Search Report for EP Application No. 19767965.7 dated Oct. 21, 2020.

International Search Report and Written Opinion for PCT Application No. PCT/US2019/022229 dated Jun. 7, 2019.

Non-Final Office Action for U.S. Appl. No. 16/980,761 mailed Aug. 21, 2023.

* cited by examiner

SYSTEMS AND METHODS FOR GENERATING BIOMARKERS BASED ON MULTIVARIATE MRI AND MULTIMODALITY CLASSIFIERS FOR DISORDER DIAGNOSIS

CROSS-REFERENCE TO RELATED APPLICATIONS

This application is a continuation of U.S. application Ser. No. 16/980,761 filed Sep. 14, 2020, which is the National Stage of International Application No. PCT/US2019/022229 filed Mar. 14, 2019, which claims the benefit of U.S. Provisional Application No. 62/642,782 filed Mar. 14, 2018 and U.S. Provisional Application No. 62/737,471 filed Sep. 27, 2018. The entirety of each of these applications is hereby incorporated by reference for all purposes.

STATEMENT REGARDING FEDERALLY SPONSORED RESEARCH OR DEVELOPMENT

This invention was made with government support under NS105944 awarded by the National Institutes of Health. The government has certain rights in the invention.

BACKGROUND

Neurodegenerative diseases can inflict differential effects across a variety of brain structures and circuits and can cause different kinds of molecular and microstructural changes within neuroanatomic systems. Diagnosis is currently made on clinical grounds but can be challenging. Generally, misdiagnosis of Parkinson's disease (PD) is a problem in patient care and in clinical trials. Accurate, objective biomarkers are lacking, and they are urgently needed to assist diagnosis and clinical trial design. Most attempts at developing biomarkers for neurodegenerative disorders have been univariable and therefore generally do not capture the complex and distinct multi-system biologies of neurodegenerative diseases. Further, biomarker studies can be expensive and time consuming to conduct.

SUMMARY

Thus, there is a need for more efficient biomarkers and related classifiers that can more efficiently and accurately classify neurodegenerative disorders in a subject.

The disclosure relates to systems and methods that can automatically classify neurodegenerative disorder(s) and/or movement disorder(s) of a subject (e.g., a subject) using at least quantitative features associated with one or more regions of interest determined from one or more sets of image data of the subject's brain. This can improve diagnosis and thus can improve patient care and costs. Additionally, biomarkers that can be automatically and be reproducibly determined can also improve the cost- and time-efficiency of therapeutic clinical trials, as they can be used as objective tools for subject selection and outcome measurement. This can increase the odds of success in such trials.

In some embodiments, the methods may include a computer-implemented method for classifying neurodegenerative disorder(s) and/or movement disorder(s) of a subject. In some embodiments, the method may include receiving subject data of a subject. The subject data may include one or more sets of MRI image data of a brain of the subject. The method may include processing one or more sets of MRI image data to extract one or more quantitative features for one or more regions. The one or more quantitative features for one or more regions may include a first quantitative feature for the one or more regions and a second quantitative feature for the one or more regions. The method may include classifying at least the one or more quantitative features for the one or more regions into one or more classes associated with neurodegenerative dementia disorder, non-neurodegenerative movement disorder, neurodegenerative movement disorder, and/or heathy control. In some embodiments, the one or more classes may include one or more stages one or more of the disorders. The method may further include generating a report including a classification of at least the one or more quantitative features. The one or more quantitative features may result in a classification of a disease/condition, as well as a differentiation between diseases/conditions.

In some embodiments, the systems may include a system for classifying neurodegenerative disorder(s) and/or movement disorder(s) of a subject. The system may include at least one processor and a memory. The processor may be configured to cause processing one or more sets of MRI image data of a brain of the subject to extract one or more quantitative features for one or more regions. The one or more quantitative features for one or more regions may include a first quantitative feature for the one or more regions and a second quantitative feature for the one or more regions. The processor may be further configured to cause classifying at least the one or more quantitative features for the one or more regions into one or more classes associated with neurodegenerative dementia disorder, non-neurodegenerative movement disorder, neurodegenerative movement disorder, and/or heathy control. In some embodiments, the one or more classes may include one or more stages of one or more of the disorders. The processor may be further configured to cause generating a report including a classification of at least the one or more quantitative features. The one or more quantitative features may result in a classification of a disease/condition, as well as a differentiation between diseases/conditions.

In some embodiments, the disclosure also relates to a computer readable media configured to classify neurodegenerative disorder(s) and/or movement disorder(s) of a subject (e.g., a subject) using at least quantitative features associated with one or more regions of interest determined from one or more sets of image data of the subject's brain. In some embodiments, the computer readable media may include a non-transitory computer readable medium storing instructions, executable by a processor, for classifying neurodegenerative disorder(s) and/or movement disorder(s) of a subject. The instructions may include processing one or more sets of MRI image data of a brain of the subject to extract one or more quantitative features for one or more regions. The one or more quantitative features for one or more regions may include a first quantitative feature for the one or more regions and a second quantitative feature for the one or more regions. The instructions may include classifying at least the one or more quantitative features for the one or more regions into one or more classes associated with neurodegenerative dementia disorder, non-neurodegenerative movement disorder, neurodegenerative movement disorder, or heathy control. In some embodiments, the one or more classes may include one or more stages associated of one or more of the disorders. The instructions may include generating a report including a classification of at least the one or more quantitative features. The one or more quantitative features may result in a classification of a disease/condition, as well as a differentiation between diseases/conditions.

In some embodiments, the one or more classes associated with neurodegenerative dementia disorder may include parkinsonian and non-parkinsonian, and/or the one or more classes associated with neurodegenerative movement disorder may include parkinsonian.

In some embodiments, the parkinsonian class for neurodegenerative dementia disorder may include one or more parkinsonian neurodegenerative dementia subclasses. The one or more parkinsonian neurodegenerative dementia subclasses may include Parkinson's disease dementia (PDD), dementia with Lewy bodies (DLB), and/or other atypical parkinsonism dementia disorder subclass. In some embodiments, the atypical parkinsonism dementia disorder subclass may include multiple system atrophy (MSA), progressive supranuclear palsy (PSP), and/or corticobasal degeneration (CBD).

In some embodiments, the non-neurodegenerative class for non-neurodegenerative movement disorder may include one or more non-neurodegenerative movement disorder subclasses. The one or more non-neurodegenerative movement disorder subclasses may include psychogenic, essential tremor, and/or drug-induced.

In some embodiments, the parkinsonian movement disorder class may include one or more parkinsonian movement disorder classes. The one or more parkinsonian movement disorder classes may include PD and/or other atypical parkinsonism. In some embodiments, the atypical parkinsonism movement disorder subclass may include MSA, PSP, and/or CBD.

In some embodiments, the MRI image data may be acquired using one or more stored protocols.

In some embodiments, the one or more quantitative features may include NM-MRI feature(s), R2* feature(s), QSM feature(s), diffusion MRI feature(s), MR spectroscopy feature(s), hyperpolarized MRI feature(s), functional MRI feature(s). and/or other sequence feature(s).

In some embodiments, the one or more regions may include one or more of the following: substantia nigra pars *compacta* (SNc), locus coeruleus (LC), subthalamic nucleus, red nucleus, globus pallidus (total, pars interna and/or pars externa), putamen (lateral, medial, and/or total), caudate, cerebellar dentate nucleus, substantia nigra pars reticulata, middle cerebellar peduncle, superior cerebellar peduncle, hippocampus (individual subfields and/or total), entorhinal cortex, parahippocampal gyrus, occipital cortex (primary visual cortext, visual association cortext, and/or total), parietal cortex, cingulate gyrus, and/or frontal cortext (M1, premotor, supplementary motor area, Broca's area, prefrontal, orbitofrontal, inferolateral frontal, and/or total).

In some embodiments, the first quantitative feature and the second quantitative feature may be based on different imaging protocols.

In some embodiments, the first quantitative feature and the second quantitative feature may be determined for different regions of the brain.

In some embodiments, the subject data may include additional subject data that is different from the one or more sets of medical image data. The classifying may also be based on one or more features extracted from the additional subject data.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIG. 7A shows a ROC curve for the classification and FIG. 7B shows as a box plot for the classification; FIG. 8A shows a ROC curve for the classification and FIG. 8B shows as a box plot for the classification.

DESCRIPTION OF THE EMBODIMENTS

Figure 1:
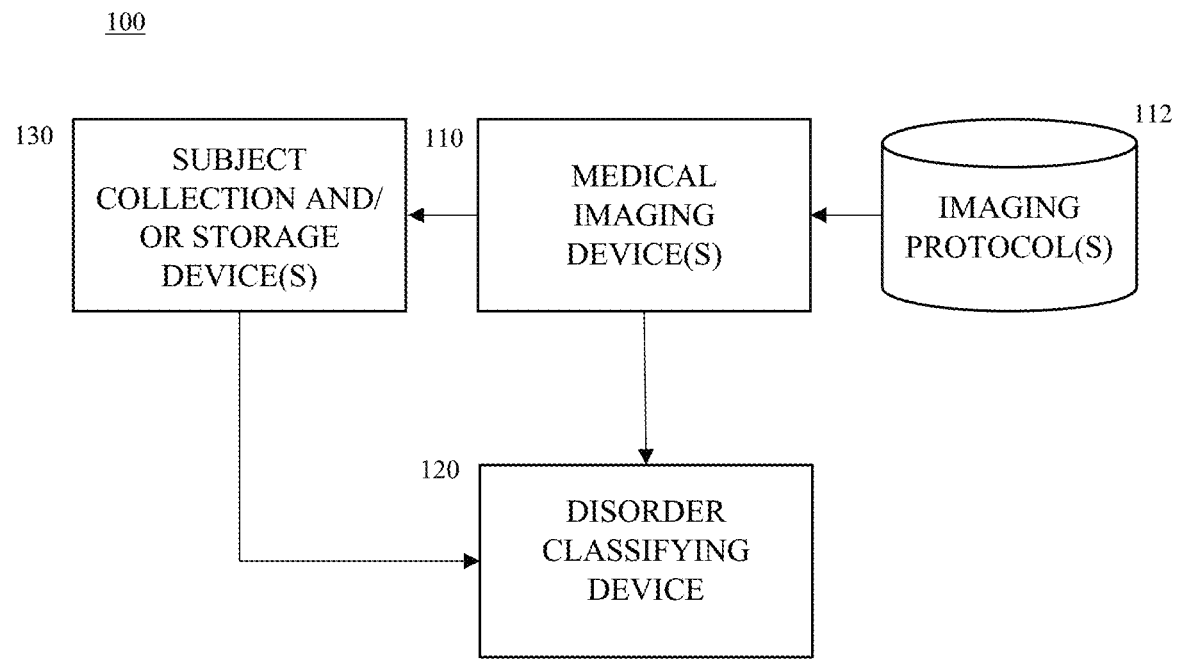
FIG. 1 shows an example of classifying a neurodegenerative and/or movement disorder using at least one or more quantitative features according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

In some embodiments, the systems and methods of the disclosure can efficiently and accurately classify neurodegenerative disorder(s) and/or movement disorder(s) of a subject (e.g., a subject), and/or more stages associated with the neurodegenerative disorder(s) and/or the movement disorder(s), using at least quantitative features, such as quantitative MRI feature(s) or measure(s), associated with one or more regions of interest determined from one or more sets of image data of the subject's brain. In some embodiments, one or more features from other subject data, such as other image data, physiological data, clinical data, demographic data, epigenetic data, omics data, among others, or any combination thereof, may also be used. In some embodiments, the systems and method can generate biomarker profiles of one or more features (biomarkers), e.g., tremor or cognitive deficits, associated with neurodegenerative disorders and/or movement disorders.

The classification results may be used to assist clinical diagnosis of Parkinson's disease, and to aid clinicians in differentiating between parkinsonian and non-parkinsonian disorders. For example, the classifier may be configured for (i) the differential diagnosis of parkinsonian disorder vs. other (non-neurodegenerative) movement disorders or (ii) the differential diagnosis of parkinsonian vs. non-parkinsonian neurodegenerative dementia disorders. In another example, the classifier may be configured for (i) the detection of a prodromal neurodegenerative disease or (ii) the differential diagnosis of prodromal neurodegenerative disease (e.g., prodromal Parkinson's disease) vs. non-prodromal neurodegenerative disease.

The classification results may include a baseline prediction of rate of future conversion to symptomatic neurodegenerative disease.

In some embodiments, the classification results may be used for detecting and quantitative monitoring of disease progression. The classification results can also be used as companion diagnostics to guide targeted therapy (e.g., i.e., personalized medicine).

The classification results may also be used for example, for research applications, including subject selection for clinical trials and outcome measurement in clinical trials. Classification results may also be used to select disease subtypes based on a desired biomarker profile. This may enable biomarker directed clinical trial designs or ultimately biomarker targeted selection of therapeutics for individual patients (i.e., subjects).

In some embodiments, the disorder(s) may include a neurodegenerative (dementia) disorder, a movement disorder (e.g., non-neurodegenerative, neurodegenerative, etc.), a sub-type of the neurodegenerative disorder or movement disorder, a stage of the neurodegenerative or movement disorder, among others, or any combination thereof.

By way of example, the neurodegenerative dementia disorders can include but are not limited to Parkinson's disease (PD), Alzheimer's disease, frontotemporal Dementia (FTD), vascular related dementia, dementia with Lewy bodies, progressive supranuclear palsy (PSP), among others, or any combination thereof. The non-neurodegenerative motor disorder sub-types may include but are not limited to healthy, psychogenic, essential tremor, drug-induced, among others, or any combination thereof. In some embodiments, the neurodegenerative motor disorder may include but is not limited to a parkinsonian disorder. The sub-types of a parkinsonian movement disorder may include parkinsonian and atypical parkinsonian movement disorder (e.g., multiple system atrophy (MSA) (e.g., parkinsonian type (MSA-P), cerebellar type (MSA-C), corticobasal degeneration (CBD), progressive supranuclear palsy (PSP), etc.) among others, or any combination thereof). In some embodiments, the parkinsonian dementia sub-types may include but are not limited to Parkinson's disease dementia (PDD), dementia with lewy bodies (DLB), other atypical parkinsonian disorders, among others, or any combination thereof. For example, the other atypical parkinsonian disorders may include but are not limited to multiple system atrophy (MSA) (e.g., parkinsonian type (MSA-P), cerebellar type (MSA-C), etc.), corticobasal degeneration (CBD), progressive supranuclear palsy (PSP), among others, or any combination thereof.

The one or more stages may include a prodromal group that may convert to symptomatic synucleinopathy, such as PD, DLB, MSA. By way of example, a prodromal group may include one or more or of idiopathic rapid-eye-movement sleep behavior disorder (iRBD), other prodromal group(s) (e.g., LRRK2 mutation carriers, GBA mutation carriers, individuals with olfactory loss, combinations of these features with iRBD, etc.), among others, or any combination thereof.

In some embodiments, the one or more sets of image data may include image data that can provide a measurable indicator of a neurological state or condition. For example, the image data can include but is not limited to image data of the brain of the subject acquired by the system using one or more stored protocols. In some embodiments, the protocols may relate to protocols for MR imaging system to acquire one or more sets of image data. For example, the protocols include but are not limited to protocols for pulse sequences for neuromelanin-sensitive MRI (e.g., explicit or incidental magnetization transfer contrast-based); iron-sensitive MRI sequences (e.g., T2 weighted imaging, R2* imaging, susceptibility weighted imaging, quantitative susceptibility mapping (QSM), etc.); diffusion MRI; resting and task-based functional MRI; chemical shift imaging; proton density imaging; spin-lattice MRI; hyperpolarized $C^{13}$ MRI (or other hyperpolarizable nuclei); intravenous contrast enhanced MRI (e.g., gadolinium, iron based contrast, other ferromagnetic contrasts, contrasts relating to non-$H^1$ based MRI such as phosphorus or fluorine, etc.); among others; or any combination thereof.

In some embodiments, the methods and systems may process the MRI pulse sequence data to determine one or more quantitative features associated with one or more regions of interest. The one more quantitative features (e.g., quantitative MRI feature(s) (can also be referred to as quantitative MRI measure(s)) may be associated with one or more regions of interest of the brain. The one or more regions of interest may include but are not limited to one or more subregions and/or the region of substantia nigra pars *compacta* (SNc), locus coeruleus (LC), subthalamic nucleus, red nucleus, globus pallidus (total, pars interna and/or pars externa), putamen (lateral, medial, and/or total), caudate, cerebellar dentate nucleus, substantia nigra pars reticulata, middle cerebellar peduncle, superior cerebellar peduncle, a hippocampus (individual subfields and/or total), entorhinal cortex, occipital cortex (primary visual cortext, visual association cortext, and/or total), parietal cortex, cingulate gyrus, parahippocampal gyrus, frontal cortex (M1, premotor, supplementary motor area, Broca's area, prefrontal, orbitofrontal, inferolateral frontal, and/or total), among others, or any combination thereof. By way of example, the one or more quantitative features may include one or more measurements determined from the one or more sets of image data related to but are not limited to NM-MRI feature(s), R2* feature(s), QSM feature(s), diffusion MRI feature(s), MR spectroscopy feature(s), hyperpolarized MRI feature(s), functional MRI feature(s), other sequence feature(s), among others, or any combination thereof. By way of example, the one or more quantitative features may include but are not limited to one or more of the following: NM-MRI volume of SNc and LC; NM-MRI, R2*, and/or QSM contrast of entire SNc and lateral-ventral SNc; NM-MRI, R2* and/or QSM contrast of the T2-weighted MRI-defined substantia nigra pars reticulate; R2* and/or QSM contrast in the cerebellar dentate nucleus; among others; or any combination thereof.

"Physiological data" can include data obtained by measuring one or more aspects of a subject's physiology. Examples of physiological data can include but are not limited to measurements of a subject's blood chemistry, including measurements of cortisol or other hormones; measurements of a subject's skin conductance response; respiratory data; and electrophysiological data, which can include electrocardiography ("ECG"), electroencephalography ("EEG"), magnetoencephalography ("MEG"), and electromyography ("EMG") measurements; other vital sign measurements (e.g., blood pressure, orthostatic vital signs, etc.), among others, or any combination thereof.

In some embodiments, the physiological data can include data acquired using personal fitness trackers or other mobile devices (e.g., smart phones, tablets, etc.) that incorporate one or more sensors including heart rate sensors, pedometers, accelerometers, temperature sensors, among others, or any combination thereof.

"Clinical data" can include about the subject that is obtained from a clinician, a subject, a computer, a mobile device (e.g., smart phones, tablets, etc.), fitness tracker, among others, including data associated with a clinical assessment, a clinical characterization, among other, or any combination thereof. In some embodiments, the clinical data may include medical history data, one or more clinical ratings, scores or scales, for example, derived from one more clinical assessment instruments, among others, or any combination thereof.

In some embodiments, the one or more clinical assessment instruments may be one or more assessments of neurocognitive assessments (e.g., that can be used to assess parkinsonian motor symptoms and/or parkinsonian non-motor symptoms). The one or more clinical assessment instruments may include one or more of questionnaires, structured neurological examinations, among others, or any combination thereof. The one or more clinical assessment instruments may be administered by and/or recorded by a clinician (or other trained individual), the patient (e.g., a self-administered questionnaire), a computer, a mobile device, among others, or any combination thereof. In some embodiments, the one or more clinical assessment instruments may use the physiological data and/or other sensor data collected during the administration (e.g., using sensors of the mobile device) of the clinical assessment instrument.

By way of example, the one or more questionnaires may include assessments of single domain areas, multi-domain areas, functioning, activities of daily living, among others, or any combination thereof. By way of example, one or more assessments of single domain areas (i.e., separate questionnaires) may include but are not limited to: depression (e.g., Beck Depression Index II), fatigue (e.g., Fatigue Questionnaire), autonomic dysfunction (e.g. SCOPA-AUT), sleep (e.g., REM Sleep Behavior Disorder Questionnaire (RBDQ), Epworth Sleepiness Scale, etc.), gait symptoms (e.g., Freezing of Gait Questionnaire (FOGQ)), among others, or any combination thereof. By way of example, one or more assessments of multiple domain areas (i.e., a single questionnaire screening multiple categories of symptoms) may include but are not limited to the Non-motor Symptoms Questionnaire (NMSQ), among others, or any combination thereof. By way of example, one or more assessments of functioning and/or daily activities may include but are not limited to the Movement Disorders Society Unified Parkinson's Disease Rating Scale Part II (MDS-UPDRS II), among others, or any combination thereof.

By way of example, the one or more structured neurological examinations performed by a clinician or other trained individuals may include but are not limited to: one or more examination components of the MDS-UPDRS Part III motor examination, the Progressive Supranuclear Palsy Rating Scale, the Unified Multiple System Atrophy Rating Scale, Montreal Cognitive Assessment, among others, or any combination thereof. In each of these cases, either individual items (e.g., single questions or tasks) may be included as separate features in analytic models, or summaries (e.g., a sum of the scores from all items in a questionnaire, such as the sum of the scores of all items in the MDS-UPDRS Part II questionnaire) may be included as separate features in analytic models.

By way of example, the one or more clinical assessment instruments that can be deployed or administered by a computer or a mobile device may include online cognitive tests. By way of another example, the one or more clinical assessment instruments that can be deployed as a software application may include one or more augmented reality applications that assess cognition or motor skills, applications that test motor function through app-based tasks, such as alternating taps, voice recording, and various measurements obtained using any combination of instructions to the patient and sensors (e.g., accelerometer and/or GPS device) (e.g., timed task of standing and walking a distance).

In some embodiments, the clinical data may include behavioral data that generally indicates a behavior of the subject. For example, the behavioral data that can be obtained from behavioral tracking of the subject. For example, the behavioral data may include data obtained from eye tracking, facial feature analysis, among others, or any combination thereof.

"Genetic data" can include data associated with genetic influences on a subject's gene expression. For example, the genetic data can include allelic variants or single nucleotide polymorphisms that identify imaging endophenotypes associated with clinical features.

"Epigenetic data" can include data associated with heritable phenotype information that do not involve alternations in the DNA sequence. For example, the epigenetic data may include data related to methylation sites, histone proteins, suprastructural aspects of DNA conformations, among others, or any combination thereof.

"Omics data" can include data associated with profiles a biological organism via detailed analysis of particular biological structures or systems. For example, the omics data may include data, such as those obtained with metabolomics, proteomics, lipidomics, genomics, transcriptomics, immunomics, metals profiling, among others, or any combination thereof.

"Other image data" may include structural or anatomical images or data acquired with MRI or other medical imaging modalities, such as positron emission tomography ("PET") or single photon emission computed tomography ("SPECT").

As used herein, "biomarker" may relate to a measurable indicator of a neurological or movement condition, whether of a normal or healthy neurological state or condition, or of a state or condition related to a neurodegenerative dementia disorder and/or movement disorder. The biomarkers described here can generally be based one or more quantitative features associated with one or more regions of interest using the image data but can also be based on features from other subject data, such as other image data, clinical data, physiological data, genetic data, epigenetic data, omics data, among others, or any combination thereof.

FIG. 1 shows a system 100 that can diagnosis a neurodegenerative disorder and/or movement disorder by classifying at least one or more quantitative features for one or more regions of interest determined from one or more sets of the image data of the brain according to embodiments. In some embodiments, the system may include a disorder classifying device 120 configured to use one or more classifiers to diagnosis a neurodegenerative disorder and/or movement disorder by classifying at least the one or more quantitative features or measures.

The disorder classifying device 120 may be configured to determine one or more quantitative features for one or more regions of interest and use one or more classifiers to perform multi-class classification of movement and/or neurodegenerative disorder using at least the one or more quantitative features for the one or more regions of interest. For example, the disorder classifying device 120 may be configured to use one or more classifiers to classify the features and diagnose the subject as 1) having movement disorder and/or 2) having neurodegenerative dementia; or 3) normal (e.g., healthy) with respect to the movement and/or neurodegenerative disorder. In some embodiments, the disorder classifying device 120 may be configured to classify the features and diagnose the subject as having a stage of a movement or neurodegenerative dementia (e.g., prodromal).

For example, with regards to the movement disorder, the classifying device 120 may be configured to use one or more classifiers to classify the feature(s) to diagnosis a subject as i) having a non-neurodegenerative movement disorder; ii) having a parkinsonian movement disorder; or 3) normal (e.g. healthy). In some embodiments, the classifying device 120 may be further configured to implement one or more classifiers to classify within these classes (subclasses). For example, for non-neurodegenerative movement disorder, the device 120 may be configured to determine whether the subject corresponds to the one or more of the following classes: psychogenic, essential tremor, drug-induced, among others, or any combination thereof. For parkinsonian movement disorder, the device 120 may be configured to determine whether the parkinsonian disorder can be PD or atypical parkinsonism. In some embodiments, the device 120 may be further configured to further classify the feature(s) associated with atypical parkinsonism into one or more sub-classes. For example, the device may be configured to classify the atypical parkinsonism movement disorder as: MSA, PSP, or CBD. In some embodiments, the device 120 may be further configured to classify MSA as either MSA-P or MSA-C.

By way of another example, with regards to the neurodegenerative dementia, the device 120 may be configured to use one or more classifiers to classify a subject as i) having a non-parkinsonian disorder; ii) having a parkinsonian disorder; or iii) normal (i.e., healthy). In some embodiments, the classifying device 120 may be configured to further classify these classes (subclasses). For example, for non-neurodegenerative disorder, the device 120 may be configured to determine whether the subject corresponds to the one or more of the following classes: AD, FTD, Vascular, among others, or any combination thereof. For parkinsonian dementia disorder, the device 120 may be configured to determine whether the parkinsonian disorder can be PD, DLB, or one or more other atypical parkinsonism subclasses. In some embodiments, the device 120 may be further configured to further classify the one or more other atypical parkinsonism subclasses. For example, the device may be configured to classify the other atypical parkinsonism disorder as either MSA, PSP, or CBD. In some embodiments, the device 120 may be further configured to classify MSA as either MSA-P or MSA-C.

In some embodiments, the system 100 may include one or more medical imaging devices 110 configured to acquire at least one or more sets of image data of a brain of the subject using one or more stored protocols 112.

In some embodiments, the medical imaging device(s) 110 may include one or more MRI systems, such as a 3T MRI scanner system. The imaging devices 110 may be configured to acquire NM-MRI related data using NM-MRI protocols, for example, the stored protocols 112.

In some embodiments, the stored protocols 112 may include: a neuromelanin-sensitive MRI pulse sequence with a reduced flip angle explicit magnetization transfer preparation pulse; a multi-echo gradient echo MRI pulse sequence suitable for acquisition of R2* and quantitative susceptibility mapping data; a diffusion protocol; among others; or any combination thereof. In some embodiments, the device 120 may determine the one or more protocols for the image acquired by the one or more medical imaging device(s) 110.

In some embodiments, the system 100 may include one or more other subject collection and/or storage devices 130 configured to collect and/or store the image data acquired by the one or more medical imaging device(s), (additional) subject data (such as physiological data, clinical data, epigenetic data, omics data, among others, or any combination thereof), among others, or any combination thereof. In some embodiments, the image data and/or (additional) subject data may be annotated with other data, such as clinical/phenotypic data.

In some embodiments, the subject data, including the one or more sets of image data as well as the other subject data, may be stored on a healthcare record system (e.g., electronic medical record system, radiological image storage (e.g., Picture Archiving and Communication System (PACS), etc.). The system 100 may be additionally and/or alternatively configured to retrieve the relevant subject data from the healthcare record system.

In some embodiments, the device 120 may be configured to process the raw MRI data to determine one or more regions of interest and related quantitative feature(s). For example, the one or more regions of interest may include but are not limited to one or more subregions and/or the region of SNc, LC, subthalamic nucleus, red nucleus, globus pallidus (total, pars interna and/or pars externa), putamen (lateral, medial, and/or total), caudate, cerebellar dentate nucleus, substantia nigra pars reticulata, middle cerebellar peduncle, superior cerebellar peduncle, hippocampus (individual subfields and/or total), entorhinal cortex, occipital cortex (primary visual cortext, visual association cortext, and/or total), parietal cortex, cingulate gyrus, parahippocampal gyrus, frontal cortext (M1, premotor, supplementary motor area, Broca's area, prefrontal, orbitofrontal, inferolateral frontal, and/or total), among others, or any combination thereof.

By way of example, the one or more quantitative features for one or more region of interest may include but are not limited to NM-MRI feature(s), R2* feature(s), QSM feature(s), diffusion MRI feature(s), MR spectroscopy feature(s), hyperpolarized MRI feature(s), and functional MRI feature(s), other sequence feature(s), among others, or any combination thereof. For example, the one or more quantitative features for one or more regions of interest may include but are not limited to one or more of the following: NM-MRI volume SNc and/or LC; NM-MRI, R2*, and/or QSM contrast of entire SNc and/or lateral-ventral SNc; NM-MRI, R2* and/or QSM contrast of the T2-weighted MRI-defined substantia nigra pars reticulate; R2* and/or QSM contrast in the cerebellar dentate nucleus; among others; or any combination thereof.

In some embodiments, the device 120 may be configured to classify a subject as having a movement and/or neurodegenerative disorder based on at least one or more quantitative features (and optionally the other subject feature(s)) using one or more classifiers. In some embodiments, the device may store one or more classifiers. Each classifier may be a machine-learning trained multivariate classifier. In some embodiments, one or more classifiers may be a binary classifier incorporating at least the one or more quantitative features. The classifier(s) may also incorporate one or more features extracted from the (other) subject data (e.g., physiological data, clinical data, epigenetic data, other image data, etc.). In some embodiments, the classifier(s) may be trained using (i) one or more machine-learning algorithms and (ii) at least the quantitative features of subjects having the movement and/or neurodegenerative disorder and subjects without the disorder(s).

In some embodiments, each classifier may be configured to classify between, within (e.g., subclasses), and/or stage(s) (e.g., prodromal) the disorders (e.g., movement and/or neurodegenerative) and normal. By way of example, at least one classifier (e.g., generated using an iRBD dataset and a control dataset) can be configured to differentiate the MRI/multimodal signature of prodromal synucleinopathy from controls; at least one classifier (e.g., generated using a PSP dataset and a PD dataset) can be configured to differentiate the MRI/multimodal signature of PSP from PD; and at least one classifier (e.g., generated using a DLB dataset and an AD dataset) can be configured to differentiate the MRI/multimodal signature of DLB from AD. The device 120 may store additional classifiers configured to classify between, within (e.g., subclasses), and/or stage(s) (e.g., prodromal) the disorders (e.g., movement and/or neurodegenerative) and normal.

In some embodiments, the device 120 may select the one or more classifiers based on inputted data, user input, stored pathways (e.g., decision tree), or any combination thereof.

In some embodiments, the one or more quantitative features may include any number of features for any number of regions of interest. In some embodiments, the one or more quantitative features may include one or more NM-MRI feature associated with one or more regions and one or more R2* features associated with one or more features. In some embodiments, the one or more quantitative features may include additional quantitative feature(s), region(s) of interest, among others, or any combination thereof.

For example, each machine learning classifier may be trained using one or more machine learning algorithms. The one or more algorithms may include but are not limited to logistic regression with elastic net, support vector machines, artificial neural networks (such as convolutional neural networks, Bayesian classifiers, and ensemble methods, etc.), other available machine learning algorithms, among others, or any combination thereof.

In some embodiments, the one or more classifiers may use a decision tree approach for differential diagnosis. For example, the classifier(s) may be configured to sequentially differentiate groups using multiple classifiers in sequence, moving from broad category diagnosis (e.g., parkinsonism vs. no parkinsonism), to narrower category (e.g., within parkinsonism, PD vs. atypical parkinsonism), to a more specific diagnosis (e.g., within atypical parkinsonism, multiple system atrophy (MSA) vs. progressive supranuclear palsy (PSP), etc.). As additional datasets are acquired (e.g. from other neurodegenerative conditions, such as Alzheimer's disease), additional nodes can be added to this decision tree to provide additional diagnostic information.

In some embodiments, the classifier device 120 may use the classification results to evaluate treatment response and/or monitor patients over time. For example, the classification can be repeated to track progression of disease (e.g., before and/or after treatment is initiated), by the device 120 repeating the classification, using one or more classifiers, at different time intervals using the same type of data and/or different data. In some embodiments, the device 120 may be configured to quantitatively monitor the disease progression. By way of example, the device may track the classification using at least one or more NM-MRI features (e.g., lateral-ventral SNc magnetization transfer contrast) over time to monitor the progression of disease in that patient. This can help determine whether a treatment therapy has been helping to prevent neurodegeneration.

In some embodiments, the device 120 may be configured to generate the one or more classifiers, for example, using the one or more quantitative features, the medical image data and/or (additional) subject data retrieved and/or stored on the storage devices 130, among others, or any combination thereof. In some embodiments, the one or more classifiers may be generated using data from a range of specific subject/patient groups to apply to specific clinical and translational applications. By way of example, classifiers can be generated from MRI and multimodality datasets collected from subject-groups of interest. MRI datasets can include but are not limited to neuromelanin-sensitive MRI and iron-sensitive MRI (e.g., R2*, QSM, SWI, etc.) acquisitions and feature extractions to quantify neurodegeneration in multiple different diseases and at different stages of disease, or longitudinally over time. In some embodiments, the one or more classifiers may be trained using datasets from the diseases and stages of interest, which can be cross-sectional or longitudinal. These datasets may also be used by the device 120 to test and validate the one or more classifiers.

In some embodiments, the one or more other collection and/or storage devices 130 and/or the classifying device 120 may be cloud-based. By way of example, the one or more imaging devices 110 may acquire the image data of a patient (e.g., with an MRI system) and cause the image data to upload to a cloud-based database, e.g., one or more other subject collection and/or storage devices 130. In this example, the one or more other subject collection and/or storage devices 130 can interface with the cloud-based classifying device 120 that includes software which executes image processing and feature extraction followed by execution of one or more classifiers to generate a report providing the (diagnostic) classification information and quantitative measures of neurodegenerative pathology. The report can inform diagnostic assessments.

In some embodiments, the devices 120 and/or 130 may include one or modules, such as containers. By way of example, the device 132 may include one or more containers for each classifier. The end-user can select from a wide range of applications (e.g., diagnosis), and modules for different classifiers can be then automatically selected as different options such that the appropriate image processing, feature selection and classifier(s) can be applied to perform the desired analysis relevant to the application of interest. Containerized modules for each of these elements and sub-processes within each element can be maintained in a software structure that is manipulated easily in a cloud-based platform. This way manipulations can occur instantly at a scale that can accommodate high volume clinical and research scan workloads.

In some embodiments, the devices 110, 120, and/or 130, as well as the stored protocols 112, may be disposed within the same device or otherwise have connectivity via a communication network. By way of example, the communication network of system 100 can include one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, NFC/RFID, RF memory tags, touch-distance radios, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Although the systems/devices of the system 100 are shown as being directly connected, the systems/devices may be indirectly connected to one or more of the other systems/devices of the system 100. In some embodiments, a system/device may be only directly connected to one or more of the other systems/devices of the system 100.

It is also to be understood that the system 100 may omit any of the devices illustrated and/or may include additional systems and/or devices not shown. It is also to be understood that more than one device and/or system may be part of the system 100 although one of each device and/or system is illustrated in the system 100. It is further to be understood that each of the plurality of devices and/or systems may be different or may be the same. For example, one or more of the devices of the devices may be hosted at any of the other devices.

Figure 4:
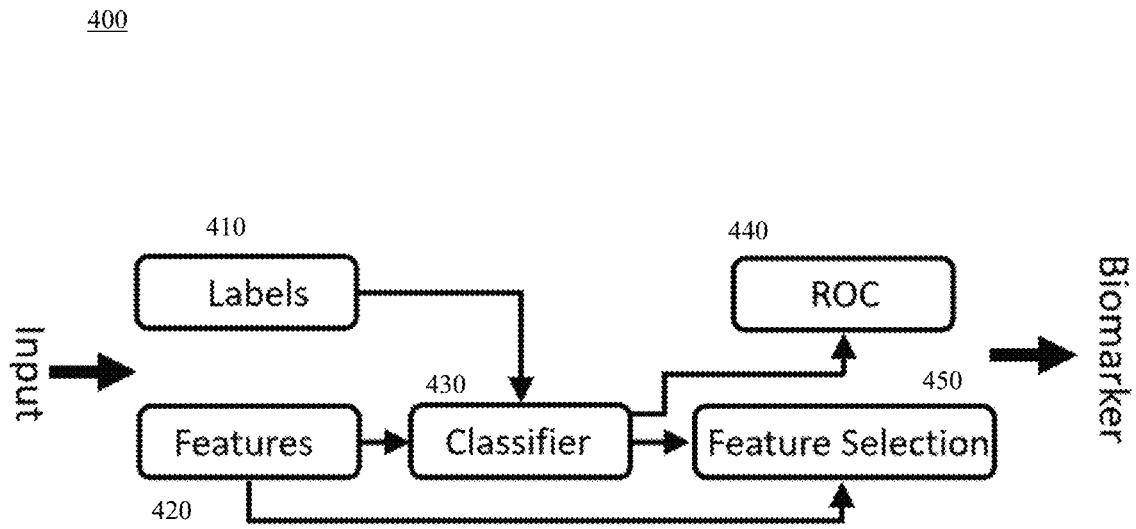
FIG. 4 shows an example of a method of generating one or more classifiers to identify biomarkers according to embodiments.

In some embodiments, any of the devices of the system 100, for example, the device 120, may include a non-transitory computer-readable medium storing program instructions thereon that is operable on a user device. A user device may be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, wearable computer (e.g., smart watch), or any combination thereof, including the accessories and peripherals of these devices, or any combination thereof. FIG. 4 shows an example of a user device.

Figure 2:
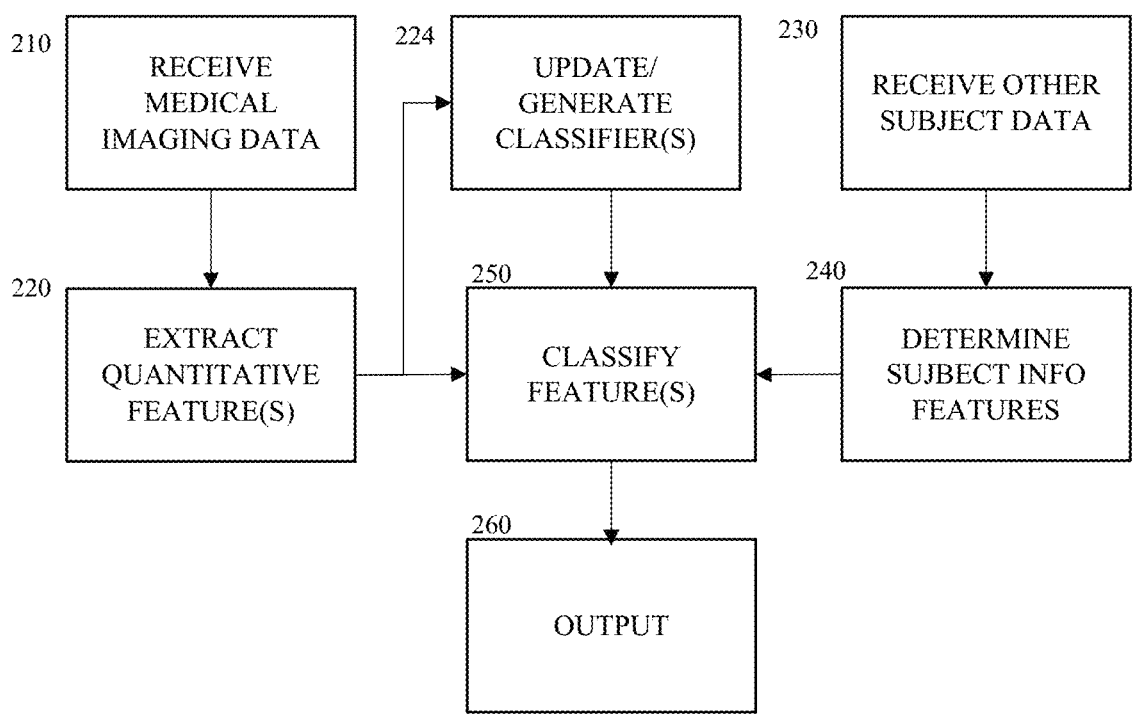
FIG. 2 shows a method of classifying a neurodegenerative and/or movement disorder using at least one or more quantitative features according to embodiments.
Figure 3:
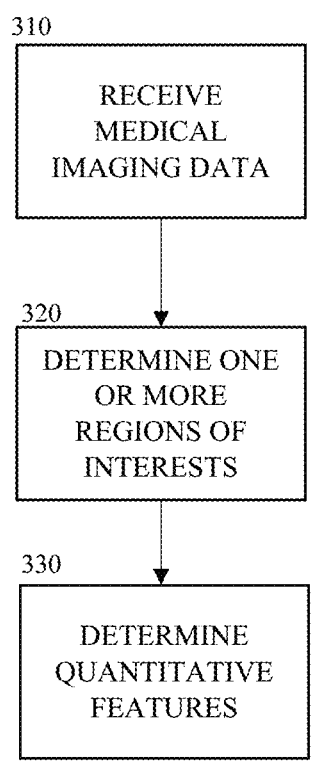
FIG. 3 shows a method of determining one or more quantitative features for one or more regions according to embodiments.

FIGS. 2 and 3 show methods of classifying a subject using at least one or more quantitative features for one or more regions of brain of the subject using one or more sets of medical image data according to embodiments and FIG. 4 shows a method of generating a classifier according to embodiments. Unless stated otherwise as apparent from the following discussion, it will be appreciated that terms such as "encoding," "generating," "determining," "displaying," "obtaining," "applying," "processing," "computing," "selecting," "receiving," "detecting," "classifying," "calculating," "quantifying," "outputting," "acquiring," "analyzing," "retrieving," "inputting," "assessing," "performing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 1 and 5. Other systems may also be used.

The methods of the disclosure are not limited to the steps described herein. The steps may be individually modified or omitted, as well as additional steps may be added. It will be also understood that at least some of the steps may be performed in parallel.

FIG. 2 illustrates a method 200 for determining a neurodegenerative and/or motion disorder based on at least one more quantitative features associated with one or more regions of the brain determined from acquired one or more sets of medical imaging of the brain. For example, the method 200 may result in a diagnosis in one of the classes and/or sub-classes described above.

In some embodiments, the method 200 may include a screening step (not shown). For example, one or more features of the clinical data may be used to screen a subject. In some embodiments, one or more features of the clinical data may be inputted into a classifier to determine whether an individual is at risk for Parkinson's disease or a related disorder (neurodegenerative disorder and/or movement disorder). For example, in practice, if the subject is determined to be at risk, the subject may need further evaluation (e.g., MRI and additional assessment) to obtain additional data for diagnostic classification shown in FIG. 2.

In some embodiments, the method 200 may include a step 210 of receiving medical image data of the subject. The medical image data may include one or more sets of MRI image data of the brain acquired using one or more stored protocols. For example, the one or more stored protocols may relate to NM-MRI, R2*, QSM, among others, or any combination thereof.

The method 200 may further include a step 220 of extracting one or more quantitative features associated with one or more regions of interest from the one or more sets of MRI image data. In some embodiments, the one or more quantitative features may include but are not limited to: NM-MRI volume; NM-MRI, R2*, and/or QSM contrast; among others; among others; or any combination thereof. In some embodiments, the one or more quantitative features may be associated with one or more of the following regions of interest: one or more subregions of and/or the region of SNc, LC, subthalamic nucleus, red nucleus, globus pallidus (total, pars interna and/or pars externa), putamen (lateral, medial, and/or total), caudate, cerebellar dentate nucleus, substantia nigra pars reticulata, middle cerebellar peduncle, superior cerebellar peduncle, hippocampus (individual subfields and/or total), entorhinal cortex, parahippocampal gyrus, occipital cortex (primary visual cortex, visual association cortex, and/or total), parietal cortex, cingulate gyrus, frontal cortex (M1, premotor, supplementary motor area, Broca's area, prefrontal, orbitofrontal, inferolateral frontal, and/or total), among others, or any combination thereof.

In some embodiments, the method 200 may optionally include a step 230 of receiving other or additional subject data, such other image data, physiological data, clinical data, demographic data, epigenetic data, among others, or any combination thereof. If the method 200 includes this step, the method may further include a step 240 of extracting one or more features from the other subject data. For example, one more features for clinical data (e.g., clinical data feature(s)) may include individual items (e.g., answers to single questions), summaries or scores for an assessment, among others, or any combination thereof.

In some embodiments, the method 200 may include a step 250 of classifying the subject based on at least the one or more quantitative features associated with one or more regions of interest using one or more classifiers. In some embodiments, the classifying 250 may also use one or more features associated with the other subject data.

In some embodiments, the one or more classifiers may be selected from a plurality of stored classifiers based on user input (e.g., those corresponding to desired analysis).

In some embodiments, each classifier may be a machine-learning trained multivariate classifier. In some embodiments, the classifier(s) may be a binary classifier incorporating at least the one or more quantitative features. The classifier(s) may incorporate one or more other subject features. In some embodiments, the classifier(s) may be trained using (i) one or more machine-learning algorithms and (ii) at least the quantitative features of subjects having the movement and/or neurodegenerative disorder and subjects without the disorder(s).

For example, the machine learning classifier(s) may be trained using one or more machine learning algorithms. The one or more algorithms may include but are not limited to logistic regression with elastic net, support vector machines, artificial neural networks (such as convolutional neural networks, Bayesian classifiers, and ensemble methods, etc.), other available machine learning algorithms, among others, or any combination thereof.

In some embodiments, the classifier(s) may use a decision tree approach for differential diagnosis. For example, the classifier(s) may be configured to sequentially classify a subject with one or more classes using multiple classifiers in sequence, moving from broad category or class diagnosis (e.g., parkinsonism vs. no parkinsonism), to narrower category or subclass (e.g., within parkinsonism, PD vs. atypical parkinsonism), to a more specific diagnosis or subclass (e.g., within atypical parkinsonism, multiple system atrophy (MSA) vs. progressive supranuclear palsy (PSP)).

In some embodiments, the method 200 may include a step 260 of outputting the results of the one or more classifiers and/or extracted features (e.g., one or more quantitative measures) for display, storage, among others, or any combination thereof. The results may include a classification of a subject with regards to the movement and/or neurodegenerative disorder (i.e., whether the individual subject has brain changes consistent with a diagnosis of Parkinson's disease). In some embodiments, the results may include a probability that the classification is correct (e.g., confidence). For example, the probability may relate to which a subject's profile (e.g., extracted features) matches the typical class (e.g., PD profile) of brain changes, based on the machine-learning trained classifier(s). The output may be presented in a customizable result report with optional graphical display of results from individual brain areas.

In some embodiments, the step 260 may include outputting the results of the classifier(s) of a specific patient for different times. This way, the results may be used to (e.g., quantitatively) monitor the progression of the disease and/or the effectiveness of medical treatment.

In some embodiments, the step 260 may include generating a visualization of the one or more quantitative measures, the classification, the medical image(s) of the subject and/or normative population control, among others, or any combination thereof. By way of example, the volumes of the SNc and the LC (e.g., generated from NM-MRI data) of the patient/subject side by side (or overlaid) with an image representing a normative population control set of SNc and LC volumes; SNc iron-sensitive contrast (e.g., R2*, QSM, SWI, and/or other T2-weighted images) of the patient/subject side by side (or overlaid) with an image representing a normative population control set of SNc iron-sensitive contrast images; iron sensitive contrast in a variety of regions implicated in atypical parkinsonian disorders, including globus pallidus, dentate nucleus of the cerebellum, putamen, caudate, subthalamic nucleus, red nucleus substantia nigra and relevant subregions within these structures, e.g. SNc, substantia nigra pars reticulata, lateral-ventral SNc side by side (or overlaid) with an image representing a normative population control set of images; diffusion MRI images of the superior cerebellar peduncle and middle cerebellar peduncles side by side (or overlaid) with an image representing a normative population control set of superior cerebellar peduncle and middle cerebellar peduncles, among others, or any combination thereof.

In some embodiments, the method 200 may include a step 224 of updating and/or generating the one or more classifiers, for example, using the extracted feature(s) (e.g., the one or more quantitative measure(s) or other subject data (e.g., longitudinal data)). As new data is acquired, which can be de-identified data, and is stored, in addition to providing desired classifications, the new data can be used to create new, larger datasets to train, test and validate the classifiers. As the datasets to train, test and validate the classifiers become larger, one or more algorithms including one or more machine-learning algorithms (such as artificial neural networks using deep learning algorithms) may be used to generate updated classifier(s). This can enable prospective improvement of the performance of the classifiers.

For example, the extracted feature(s) may be used to update the classifier(s), using a machine learning classifier device (e.g., the device 120) to develop multivariate progression marker profiles to generate improved classifier(s). These progression marker profiles may be used as outcome measures for clinical trials. The classifier may also be updated with additional MRI data from other diseases that can be difficult to differentiate from PD, in order to assist with differential diagnosis of PD. The classifier may also be updated with new diagnostic data, such as autopsy diagnosis data, to improve accuracy of the classifier.

In some embodiments, the results (e.g., the extracted feature(s) (e.g., the one or more quantitative measures(s) or subject data)) may be used to generate one or more classifiers using the machine learning classifier device (e.g., the device 120), for example, by training the classifier with the results and/or retrospective data.

FIG. 3 shows a method 300 of processing the medical image data to determine one or more quantitative features associated with one or more regions of interest. In some embodiments, the one or more quantitative features associated with one or more regions of interest can relate to the pulse sequence protocol. For example, the one more quantitative features associated with one more regions of interest may include: NM-MRI feature(s), R2* features, QSM features, Diffusion MRI features, MR spectroscopy features, hyperpolarized MRI features, functional MRI feature, among other sequence features, or any combination thereof.

In some embodiments, the method 300 may include a step 310 of receiving medical image data of the brain of the subject. In some embodiments, the medical image data may include one or more sets of MRI data acquired using one or more stored MRI protocols related to NM-MRI feature(s), R2* features, QSM features, Diffusion MRI features, among other sequence features, or any combination thereof. For example, the MRI protocol to acquire a set of MRI data associated with NM-MRI features, may include a neuromelanin-sensitive MRI pulse sequence with a reduced flip angle explicit magnetization transfer preparation pulse. See, for example, Chen X, Huddleston D E, Langley J, Ahn S, Barnum C J, Factor S A, et al. Simultaneous imaging of locus coeruleus and substantia nigra with a quantitative neuromelanin MRI approach. Magnetic resonance imaging. 2014. For example, the MRI protocol to acquire MRI data associated with R2* features, R2* and quantitative susceptibility mapping data may be a multi-echo gradient echo MRI pulse sequence suitable for acquisition of R2* and quantitative susceptibility mapping data may be a multi-echo gradient echo MRI pulse sequence. See, for example, Langkammer C, Pirpamer L, Seiler S, Deistung A, Schweser F, Franthal S, et al. Quantitative Susceptibility Mapping in Parkinson's Disease. PloS one. 2016; 11(9):e0162460.

In some embodiments, the method 300 may include a step 320 of determining one or more regions of interest using one or more sets of image data of a brain of a subject acquired using the respective protocol. For example, the step 320 may include separately processing one or more sets of image data associated with NM-MRI feature(s), R2* feature(s), QSM feature(s), diffusion MRI feature(s), and/or other sequence feature(s), to determine the one or more regions of interest.

In some embodiments, the step 320 may include segmenting one or more sets of image data into one or more regions of interest using a respective mask and/or atlas within one or more sets of image data. The masks and/or atlases may be associated with one or more regions of a brain of the subject: SNc (e.g., entire, lateral-ventral SNc, and/or medial SNc (e.g., defined as the medial 50% of the NM-MRI defined SNc determined by measurement along the long axis of the NM-MRI determined SNc in the axial plane), etc.), LC, subthalamic nucleus, red nucleus, globus pallidus (total, pars interna and/or pars externa), putamen (lateral, medial, and/or total), caudate, cerebellar dentate nucleus, substantia nigra pars reticulata, middle cerebellar peduncle, superior cerebellar peduncle, hippocampus (individual subfields and/or total), entorhinal cortex, occipital cortex (primary visual cortext, visual association cortext, and/or total), parietal cortex, cingulate gyrus, parahippocampal gyrus, frontal cortext (M1, premotor, supplementary motor area, Broca's area, prefrontal, orbitofrontal, inferolateral frontal, and/or total), among others, or any combination thereof. In some embodiments, one or more image contrasts may be used to define these masks so as to determine the location of the structure based on tissue characteristics measurable with MRI. For example, the contrasts may include but are on limited to: Iron-sensitive image datasets (R2*, QSM, susceptibility weighted imaging (SWI), or other T2-weighted contrasts) may be used for ROI masks for iron-rich structures and its subregions (e.g. caudate, putamen, globus pallidus, substantia nigra pars reticulata, subthalamic nucleus, red nucleus); neuromelanin-sensitive image datasets may be used for ROI masks for SNc and its subregions, LC, and the ventral tegmental area; diffusion MRI datasets may be used for masks for white matter tracts and structures (e.g., the superior cerebellar peduncle, middle cerebellar peduncle, brainstem oculomotor tracts, the nigrostriatal tract, and/or the dentato-rubro-thalamic tract); among others; or any combination thereof.

By way of example, to determine the SNc region and the associated NM-MRI features, a set of NM-MRI data with coverage of SNc and a set of T1-weighted structural image data may be processed. Using a region of interest (ROI) mask for SNc, the subject image data may be transformed from MNI-152 standard space to individual T1 space. For example, the T1-weighted structural image may automatically be extracted and then aligned with the MNI extracted image using an affine transformation with the FSL linear registration tool (FLIRT). Next the FSL nonlinear registration tool (FNIRT) may be used to carry out a nonlinear transformation between individual subject T1 space and common space. Then this transformation can be inverted and the SNc population ROI can be transformed back to subject T1-space. The individual's processed NM-MRI image data may be registered to the brain extracted T1-weighted image and transformed using FLIRT into T1-space. The transformed SNc population mask may be then used to select the SNc ROI.

For example, for the lateral-ventral SNc, the method described in Huddleston D E, Langley J, Sedlacik J, Boelmans K, Factor S A, Hu X P. In vivo detection of lateral-ventral tier nigral degeneration in Parkinson's disease. Human brain mapping. 2017; 38(5):2627-3, may be used. By way of another example, a substantia nigra pars reticulata (SNr), a mask similar to the one described in Langley J, Huddleston D E, Merritt M, Chen X, McMurray R, Silver M, et al. Diffusion tensor imaging of the substantia nigra in Parkinson's disease revisited. Human brain mapping. 2016; 37(7):2547-56, may be used. In another example, for the cerebellar dentate nucleus mask, a mask similar to the one described in He N, Langley J, Huddleston D E, Ling H, Xu H, Liu C, et al. Improved Neuroimaging Atlas of the Dentate Nucleus. Cerebellum. 2017; 16(5-6): 951-6, may be used.

For example, in some embodiments, one or more QSM defined group masks for subthalamic nucleus, red nucleus, globus pallidus (total, pars interna and/or pars externa), putamen, and/or caudate may be used. For the lateral putamen, a QSM defined atlas may be used, for example, that is defined as the lateral 50% of the QSM putamen group mask along its long axis in the axial plane.

After a region of interest is segmented from the set of image data, the method 300 may include a step 330 of determining or extracting one or more quantitative features associated with one or more regions of interest of a brain of a subject. In the example above, from the SNc region of interest determined using the NM-MRI data with coverage of SNc and a set of T1-weighted structural image data, the mean MTC may be determined. Additionally, SNc volume can also be determined. By way of example, after the LC is determined, the LC volume may be determined. For example, the volume may be determined using methods described in Chen X, Huddleston D E, Langley J, Ahn S, Barnum C J, Factor S A, et al. Simultaneous imaging of locus coeruleus and substantia nigra with a quantitative neuromelanin MRI approach. Magnetic resonance imaging. 2014, and Langley J, Huddleston D E, Liu C J, Hu X.

Reproducibility of locus coeruleus and substantia nigra imaging with neuromelanin sensitive MRI. MAGMA. 2017; 30(2):121-5.

For example, the nigrostriatal tract volume may be determined with tractography using the NM-MRI defined SNc and QSM defined lateral putamen as seed regions, and diffusion MRI measures in the nigrostriatal tract. Subtract volumes may also be determined using the lateral-ventral SNc ROI atlas and the medial SNc ROI atlas as seed regions.

In some embodiments, other methods may be used to determine one or more regions and/or quantitative feature(s) associated with NM-MRI feature(s), R2* feature(s), QSM feature(s), diffusion MRI feature(s), and/or other sequence feature(s). For example, other methods may be used to determine the one or more regions and/or one or more quantitative features. In some embodiments, additional, alternative, different, less and/or more feature(s) and/or region(s) may be determined. FIG. 4 shows an example of a method 400 of generating one or more classifiers to identify biomarkers, for example, using a machine learning classifying device (e.g., the device 120). By way of example, labels 410 and features 420 can be inputted into a classifier 430. For example, the classifier may use logistic regression with elastic net regularization (ENR) and 5-fold cross-validation to classify between subject groups. After classifying the subjects (step 430), the receiver operating characteristic (ROC) and the area under the curve (AUC) may be calculated in step 440. In some embodiments, the step 440 may include generating a confusion matrix, calculating the sensitivity, specificity, and/or accuracy of the classification among others, or any combination thereof. In some embodiments, the step 430 of classifying may further include a feature selection step 450. By way of example, the classifier step 430 may determine and output ENR coefficients for each feature to determine feature importance. For example, those features with higher mean ENR coefficients were considered to have greater importance than those features with lower mean ENR coefficients.

Figure 5:
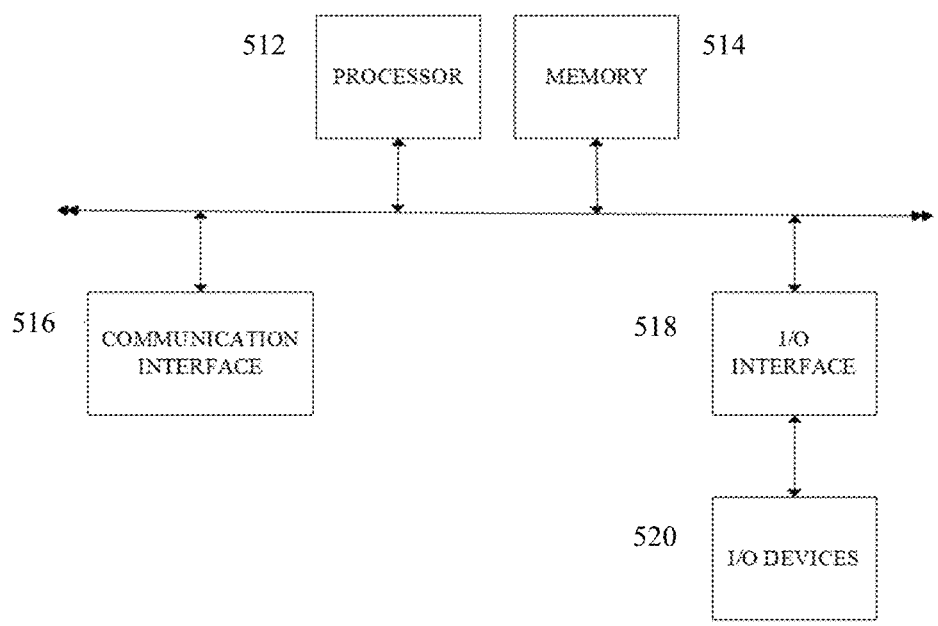
FIG. 5 shows a block diagram illustrating an example of a computing system.

One or more of the devices and/or systems of the system 100 may be and/or include a computer system and/or device. FIG. 5 is a block diagram showing an example of a computer system 400. The modules of the computer system 500 may be included in at least some of the systems and/or modules, as well as other devices and/or systems of the system 100.

The system for carrying out the embodiments of the methods disclosed herein is not limited to the systems shown in FIGS. 1 and 5. Other systems may also be used. It is also to be understood that the system 500 may omit any of the modules illustrated and/or may include additional modules not shown.

The system 500 shown in FIG. 5 may include any number of modules that communicate with each other through electrical or data connections (not shown). In some embodiments, the modules may be connected via any network (e.g., wired network, wireless network, or any combination thereof).

The system 500 may be a computing system, such as a workstation, computer, or the like. The system 500 may include one or more processors 512. The processor(s) 512 may include one or more processing units, which may be any known processor or a microprocessor. For example, the processor(s) may include any known central processing unit (CPU), graphical processing unit (GPU) (e.g., capable of efficient arithmetic on large matrices encountered in deep learning models), among others, or any combination thereof. The processor(s) 512 may be coupled directly or indirectly to one or more computer-readable storage media (e.g., memory) 514. The memory 514 may include random access memory (RAM), read only memory (ROM), disk drive, tape drive, etc., or any combinations thereof. The memory 514 may be configured to store programs and data, including data structures. In some embodiments, the memory 514 may also include a frame buffer for storing data arrays.

In some embodiments, another computer system may assume the data analysis, image processing, or other functions of the processor(s) 512. In response to commands received from an input device, the programs or data stored in the memory 514 may be archived in long term storage or may be further processed by the processor and presented on a display.

In some embodiments, the system 500 may include a communication interface 516 configured to conduct receiving and transmitting of data between other modules on the system and/or network. The communication interface 516 may be a wired and/or wireless interface, a switched circuit wireless interface, a network of data processing devices, such as LAN, WAN, the internet, or any combination thereof. The communication interface may be configured to execute various communication protocols, such as Bluetooth, wireless, and Ethernet, in order to establish and maintain communication with at least another module on the network.

In some embodiments, the system 510 may include an input/output interface 518 configured for receiving information from one or more input devices 520 (e.g., a keyboard, a mouse, and the like) and/or conveying information to one or more output devices 520 (e.g., a printer, a CD writer, a DVD writer, portable flash memory, etc.). In some embodiments, the one or more input devices 520 may be configured to control, for example, the generation of the management plan and/or prompt, the display of the management plan and/or prompt on a display, the printing of the management plan and/or prompt by a printer interface, the transmission of a management plan and/or prompt, among other things.

In some embodiments, the disclosed methods (e.g., FIGS. 2-4) may be implemented using software applications that are stored in a memory and executed by the one or more processors (e.g., CPU and/or GPU) provided on the system 100. In some embodiments, the disclosed methods may be implemented using software applications that are stored in memories and executed by the one or more processors distributed across the system.

As such, any of the systems and/or modules of the system 100 may be a general purpose computer system, such as system 500, that becomes a specific purpose computer system when executing the routines and methods of the disclosure. The systems and/or modules of the system 100 may also include an operating system and micro instruction code. The various processes and functions described herein may either be part of the micro instruction code or part of the application program or routine (or any combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 5. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

Examples

Figure 6:
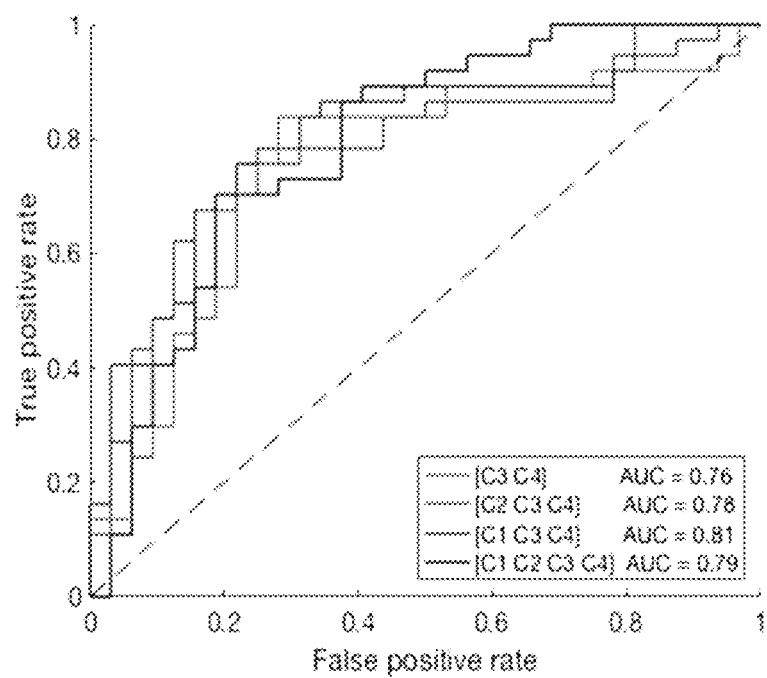
FIG. 6 shows example of a multivariate classification of Parkinson's disease using more than one quantitative measure according to embodiments.

FIG. 6 shows an example of multivariate classification of Parkinson's disease using quantitative measures of neuromelanin and iron pathology. This example is based on a study.

Aim of the Study

In previous work, an automated and highly reproducible neuromelanin-sensitive MRI (NM-MRI) approach was developed (Langley et al, 2017, PMID: 27687624) that detects Parkinson's disease (PD) effects in substantia nigra pars *compacta* (SNc) and locus coeruleus in vivo. The objective of the study was to combine this NM-MRI approach with R2* imaging, which is sensitive to iron accumulation, in order to accurately classify PD. To attempt to develop an accurate classifier, NM-MRI determined SNc volume, SNc R2*, age and gender in multivariate models was included in the study.

Method

Research was conducted under an Emory Institutional Review Board approved protocol. 35 patients with PD (UK Brain Bank Criteria) and 32 control participants were scanned using a 3T MRI scanner (Prisma, Siemens Medical Solutions, Malvern, PD, USA) with a 64 channel receive-only head coil. NM-MRI data and R2* data were acquired and processed using published methods (Langley et al, 2017, PMID: 27687624; Huddleston et al, 2017, PMID: 28240402; Barbosa et al, 2015, PMID: 25721997). Using these methods, the NM-MRI SNc volume was determined and R2* was measured in the NM-MRI defined SNc ROI. A logistic regression model with five-fold cross validation was used for multivariate classification of PD and control subjects. The area under the receiver operating characteristic curve (AUC) was used to quantify the performance of the classifier. To test the effect of different input features on the classification accuracy, logistic regression models were trained using different combinations of feature sets as the input and model performance was compared using the corresponding AUCs.

Results

FIG. 6 shows receiver operating characteristic curves and AUCs for each classification model. C1=age, C2=gender, C3=SNc volume, C4=SNc R2*.

CONCLUSION

The model including 1) NM-MRI determined SNc volume, 2) R2* in the NM-MRI defined SNc ROI and 3) age performed best for classification of PD and control individuals, with an AUC of 0.81. This multivariate profile warrants further investigation as a candidate PD biomarker.

Figure 7A:
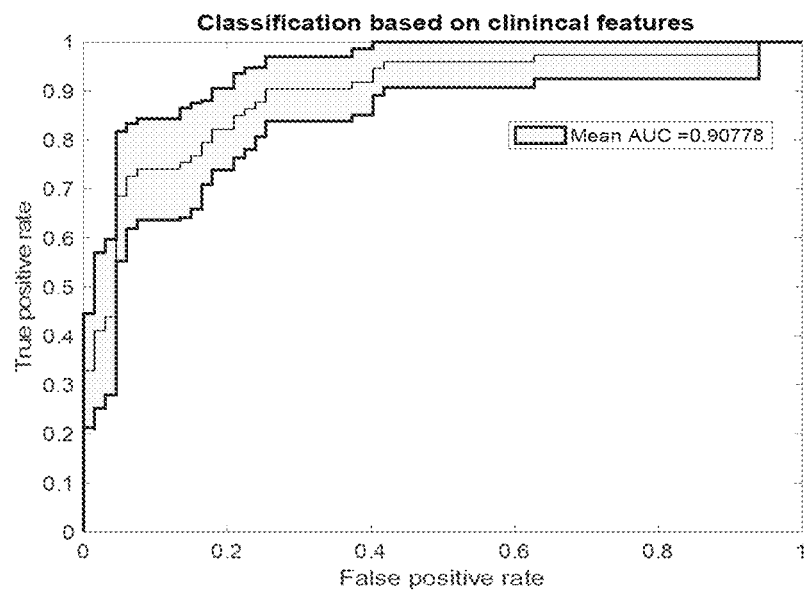
FIGS. 7A and 7B show an example of a multivariate classification of Parkinson's disease using more than one clinical feature.
Figure 7B:
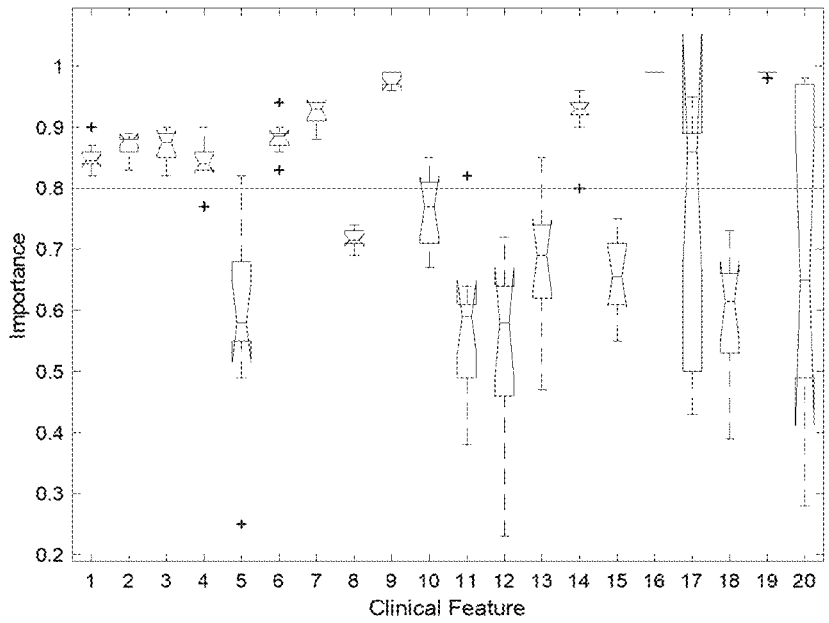
Figure 8A:
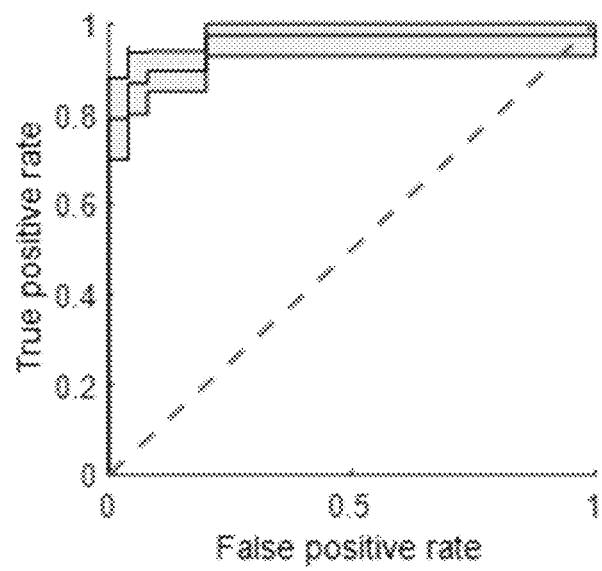
FIGS. 8A and 8B show another example of a multivariate classification of Parkinson's disease using more than one clinical feature and quantitative measure according to embodiments.
Figure 8B:
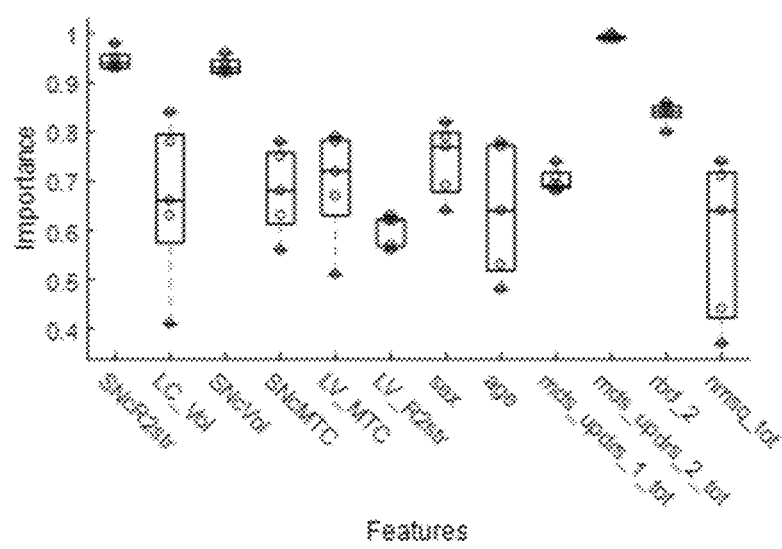

FIGS. 7A and 7B show an example of results of a classifier based only on clinical data features. For example, the classifier may be used as a screening classifier to determine risk of a neurocognitive or neurodegenerative condition (e.g., Parkinson's disease). In this example, the classifier consisted of 20 clinical features, of which the 9 most informative features were 1) heart rate lying flat, 2) heart rate standing up, 3) systolic blood pressure, 4) Questionnaire item (RBDQ item 2): Aggressive, action-packed dreams? yes/no, 5) Questionnaire item (NMSQ item 1): dribbling of saliva during daytime? yes/no, 6) Questionnaire item (NMSQ item 2): loss or change in taste or smell? yes/no, 7) Questionnaire item (NMSQ item 5): constipation or strain to pass stool? yes/no, 8) Questionnaire item (NMSQ item 20): feeling light-headed, dizzy or weak standing from sitting or lying? yes/no, 9) Questionnaire item (FOGQ item 1): During your worst state do you walk: (0) normally, (1) almost normally-somewhat slow, (2) slow but fully independent, (3) need assistance or walking aid, (4) unable to walk. This clinical classifier performed with 90.8% accuracy. FIG. 7A shows the ROC curve for the classifier used in this example. FIG. 7B shows a boxplot of the relative importance of each of the features to the classification FIGS. 8A and 8B show an example of results of a classifier using the method according to the disclosure (e.g., shown in FIGS. 2-4). In this example, a dataset composed of 12 clinical, demographic, and MRI-based features was used. In this example, the classifier combined 6 MRI features and 6 clinical features. The MRI features were collected using a Siemens Prisma-Fit 3T scanner. The MRI features (i.e., quantitative features) included neuromelanin-sensitive MRI (NM-MRI), R2* (iron-sensitive MRI), and magnetization transfer contrast (MTC) of the substantia nigra pars *compacta* (SNc) and profound locus coeruleus (LC). Specifically, the MRI features are 1) SNc volume, 2) LC volume, 3) SNc R2*, 4) SNc magnetization transfer contrast (MTC—the NM-MRI contrast), 5) lateral-ventral SNc MTC, and 6) lateral-ventral SNc R2*. The classifier also used features from data from several clinical questionnaires that included the Movement Disorders Society Unified Parkinson's Disease Rating Scale (MDS-UPDRS) Parts I and II, the REM Sleep Behavior Disorder Questionnaire (RBDQ), and the Non-Motors Symptoms Questionnaire (NMSQ); and demographic data that included age and sex. Specifically, the clinical/demographic features are 1) gender, 2) age, 3) MDS-UPDRS Part 1 questionnaire total score (Non-motor aspects of experiences of daily living), 4) MDS-UPDRS Part 2, 5) RBD-Q item 2, and 6) NMSQ total score.

FIG. 8A shows the ROC curve for the classifier used in this example. FIG. 8B shows a boxplot of the relative importance of each of the features to the classification. The accuracy of this classifier is 94.2%. As shown in FIG. 8B, the five most important features were (1) mds_updrs_2tot, (2) SNcR2str, (3) SNcVol, (4) rbd_2, and (5) sex. Aside from the top three or four features, most of the other features seemed to have comparable importance.

This diagnostic accuracy of the classifier enhances diagnostic confidence (as compared to a clinical assessment alone). The classifier can confirm and quantify neurodegenerative changes in neuromelanin and iron on MRI enhances diagnostic confidence. The incorporation of MRI features in the classifier can also better enable clinicians to convey the meaning of the test results, i.e. this can provide direct observation of the brain changes that underlie the diagnosis.

The disclosure of the references cited in the Description is hereby incorporated herein by reference in its entirety.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A computer-implemented method for classifying at least one of neurodegenerative disorder and non-neurodegenerative movement disorder of a subject, the method comprising:
receiving subject data of a subject, the subject data including a plurality of sets of MRI image data of a brain of the subject, the plurality of sets of MRI image data including neuromelanin-sensitive MRI data and iron-sensitive MRI data;
processing each set of MRI image data to extract a plurality of quantitative features for one or more regions of the brain, the plurality of quantitative features for the one or more regions includes a first quantitative feature and a second quantitative feature;
the first quantitative feature determined using the neuromelanin-sensitive MRI data; and
the second quantitative feature determined using the iron-sensitive MRI data;
classifying the subject data using the plurality of quantitative features for the one or more regions into one or more classes from a plurality of classes, the plurality of classes including neurodegenerative dementia disorder, neurodegenerative movement disorder, non-neurodegenerative movement disorder, and/or heathy control; and
generating a report including the one or more classes.

2. The method according to claim 1, wherein the neurodegenerative dementia disorder includes a parkinsonian class and a non-parkinsonian class.

3. The method according to claim 2, wherein:
the parkinsonian class for the neurodegenerative dementia disorder includes one or more parkinsonian neurodegenerative dementia subclasses; and
the one or more parkinsonian neurodegenerative dementia subclasses includes at least one of Parkinson's disease dementia (PDD), dementia with Lewy bodies (DLB), and one or more other atypical parkinsonism dementia disorder subclasses.

4. The method according to claim 3, wherein the one or more other atypical parkinsonism dementia disorder subclasses includes at least one of multiple system atrophy (MSA), progressive supranuclear palsy (PSP), and corticobasal degeneration (CBD).

5. The method according to claim 1, wherein:
the non-neurodegenerative movement disorder includes one or more non-neurodegenerative movement disorder subclasses; and
the one or more non-neurodegenerative movement disorder subclasses includes psychogenic, essential tremor, and drug-induced.

6. The method according to claim 1, wherein:
the neurodegenerative movement disorder includes a parkinsonian class;
the parkinsonian class for the neurogenerative movement disorder includes one or more parkinsonian movement disorder subclasses; and
the one or more parkinsonian movement disorder subclasses includes Parkinson's Disease (PD) and one or more other atypical parkinsonism movement disorder subclasses.

7. The method according to claim 6, wherein the one or more other atypical parkinsonism movement disorder subclasses includes at least one of MSA, PSP, and CBD.

8. The method according to claim 1, wherein:
the plurality of sets of MRI image data is acquired by one or more stored protocols, the one or more protocols including one or more protocols for iron-sensitive MRI sequences and one or more protocols for neuromelanin-sensitive MRI sequences; and
the plurality of quantitative features include (i) one or more of NM-MRI features and (ii) one or more of R2* features or one or more of qualitative susceptibility mapping (QSM) features.

9. The method according to claim 8, wherein the plurality of quantitative features also include one or more of diffusion MRI features.

10. The method according to claim 8, wherein the one or more regions includes substantia nigra pars *compacta* (SNc) and locus coeruleus (LC).

11. The method according to claim 10, wherein the one or more regions also includes at least one of red nucleus and globus pallidus.

12. A system for classifying at least one of neurodegenerative disorder and non-neurodegenerative movement disorder of a subject, the system comprising:
at least one processor; and
a memory having stored thereon computer-executable instructions which are executable by the at least one processor to cause the system to perform at least the following:
processing a plurality of sets of MRI image data of a brain of the subject to extract a plurality of quantitative features for one or more regions of the brain, the plurality sets of MRI image data including neuromelanin-sensitive MRI data and iron-sensitive MRI data, the plurality of quantitative features for the one or more regions includes a first quantitative feature and a second quantitative feature for the one or more regions;
the first quantitative feature determined using the neuromelanin-sensitive MRI data; and
the second quantitative feature determined using the iron-sensitive MRI data;
classifying the subject data using the plurality quantitative features for the one or more regions into one or more classes from a plurality of classes, the plurality of classes including neurodegenerative dementia disorder, neurodegenerative movement disorder, non-neurogenerative movement disorder, and/or heathy control; and
generating a report including the one or more classes.

13. The system according to claim 12, wherein:
the plurality of sets of MRI image data is acquired by one or more stored protocols, the one or more protocols including one or more protocols for iron-sensitive MRI sequences and one or more protocols for neuromelanin-sensitive MRI sequences; and
the plurality of quantitative features include (i) one or more of NM-MRI features and (ii) one or more of R2* features or qualitative susceptibility mapping (QSM) features.

14. The system according to claim 13, wherein the plurality of quantitative features also include one or more diffusion MRI features.

15. The system according to claim 14, wherein the neurodegenerative dementia disorder includes a parkinsonian class and a non-parkinsonian class.

16. The system according to claim 13, wherein:
the neurodegenerative movement disorder include a parkinsonian class;

the parkinsonian class for the neurodegenerative dementia disorder includes one or more parkinsonian neurodegenerative dementia subclasses; and the one or more parkinsonian neurodegenerative dementia subclasses includes at least one of Parkinson's disease dementia (PDD), dementia with Lewy bodies (DLB), and one or more other atypical parkinsonism dementia disorder subclasses.

17. The system according to claim 16, wherein the one or more other atypical parkinsonism dementia disorder subclasses includes at least one of multiple system atrophy (MSA), progressive supranuclear palsy (PSP), and corticobasal degeneration (CBD).

18. The system according to claim 13, wherein the one or more regions includes substantia nigra pars *compacta* (SNc) and locus coeruleus (LC).

19. The system according to claim 18, wherein the one or more regions also includes at least one of red nucleus and globus pallidus.

20. The method according to claim 1, wherein:
the subject data further includes at least one of clinical data, physiological data, demographic data, and genetic data;
the processing further includes processing the subject data to determine one or more clinical features; and
the classifying further includes using the one or more clinical features to classify the subject data into the one or more classes.

21. The system according to claim 12, wherein:
the subject data further includes at least one of clinical data, physiological data, demographic data, and genetic data;
the processing further includes processing the subject data to determine one or more clinical features; and
the classifying further includes using the one or more clinical features to classify the subject data into the one or more classes.

* * * * *